United States Patent [19]

Sankey et al.

[11] Patent Number: 4,704,236
[45] Date of Patent: Nov. 3, 1987

[54] PREPARATION OF SULPHOPHENYL ESTERS

[75] Inventors: John P. Sankey; William R. Sanderson, both of Warrington, England

[73] Assignee: Interox Chemicals Ltd., London, England

[21] Appl. No.: 910,967

[22] Filed: Sep. 24, 1986

[30] Foreign Application Priority Data

Sep. 28, 1985 [GB] United Kingdom ............... 8523962

[51] Int. Cl.$^4$ ..................... C11C 3/00; C07C 69/017
[52] U.S. Cl. ..................................... 260/402; 560/142
[58] Field of Search ..................... 560/142; 260/402

[56] References Cited

U.S. PATENT DOCUMENTS

| 4,536,314 | 8/1985 | Hardy et al. | 260/402 |
| 4,588,531 | 5/1986 | Balzer et al. | 560/142 |

FOREIGN PATENT DOCUMENTS

| 0125641 | 11/1984 | European Pat. Off. | 260/402 |
| 0148148 | 7/1985 | European Pat. Off. | 260/402 |
| 0164786 | 12/1985 | European Pat. Off. | 260/402 |
| 935398 | 8/1963 | United Kingdom | 560/142 |

*Primary Examiner*—J. E. Evans
*Attorney, Agent, or Firm*—Larson and Taylor

[57] ABSTRACT

Sulphophenyl esters can be made amongst other routes by reacting an acyl halide with a phenol sulphonate salt, but it has been suggested in the prior art that there are substantial problems or disadvantages associated with carrying out the reaction in the presence of an organic solvent such as gelation of the reaction medium or excessive reaction times.

In the present invention, the process employs as organic solvent high boiling point primarily aliphatic hydrocarbons which forms with linear acyl halide a reaction medium in which products of high and/or improved purity and/or yield are obtainable without gelation and in reasonable reaction periods, especially between $C_6$-$C_{10}$ linear acyl chlorides and sodium phenol sulphonate.

It has been found advantageous to pre-dry the phenol sulphonate salt by heating it when dispersed in a high boiling aliphatic or aromatic hydrocarbon solvent such that water and solvent are co-removed, with the result that in a subsequent esterification reaction with acyl halide an improvement in yield and/or purity of the sulphophenyl ester can be achieved.

12 Claims, No Drawings

PREPARATION OF SULPHOPHENYL ESTERS

The present invention relates to the preparation of sulphophenyl esters, alternatively referable to as acyloxy benzene sulphonates or alkanoyl oxybenzene sulphonates, and more particularly to an improvement or modification to a preparative process in which a carboxylic acid halide is reacted with an alkali metal phenol sulphonate.

Reaction between a sulphonated phenol in acid form and a fatty acid chloride is disclosed in U.S. Pat. No.3503888 issued on Mar. 31 1970 to the Dow Chemical Co (Miller et al). The reaction was carried out in the presence of an organic solvent, methylene chloride, in Example 1. Subsequent disclosures in patents or patent applications have drawn attention to disadvantages in the use of an acid chloride as esterifying agent for phenol sulphonates. Thus, for example in European Patent Application, Publication No. 0 105 672, published 18 Apr. 1984, Procter and Gamble suggests in the section on background technology that the use of an acyl halide in a solvent such as dioxan or dichloroethane presents significant difficulties including the fact that conversions in excess of 70% are difficult to obtain and there are difficulties in the elimination of hydrogen chloride from the reaction medium. Accordingly, Procter and Gamble proposed an alternative transesterification process despite their own recognition that there is an increased risk of side reactions and product degradation at higher reaction temperatures, which can even include extensive carbonisation of the reaction mixture.

Rather different problems with the use of acid chlorides are asserted by Rhone Poulenc Chemie in European Patent Application, Publication No. 0153223, published 28th Aug. 1985, namely that the reaction with the potassium salt is extremely slow, even at elevated temperatures and the product formed is very difficult to isolate. In addition, though, the difficulty of eliminating HCl is featured. Finally in European Patent Application Publication No. 0 148 148 published on 10th July 1985, Monsanto asserts that the use of acyl chloride in organic solvents requires long reaction times, extensive separation and clean-up procedures to obtain the product and recover the solvent and even that use of low levels of solvent can result in the formation of gelled reaction product.

Accordingly, there is within the several publications from highly respected chemical companies extensive teaching against the use of an acyl chloride in an organic solvent to esterify phenol sulphonates, despite their recognition that the method itself is a conventional one for ester formation generally.

In the course of the investigations during which the instant invention was devised, the reaction between an acyl chloride and phenol sulphonic acid or a phenol sulphonate salt was attempted in the presence of the various organic solvents referred to in the above-mentioned prior publications. To a considerable extent the disadvantages of using an organic solvent manifested themselves in these trials and confirmed that the teaching was based upon reality rather than blind prejudice. For example when excess isononanoyl chloride was boiled under reflux with sodium phenol sulphonate dispersed in 1,4-dioxan as solvent for 4 hours a yield of less than 25% product was obtained, based upon the sodium phenol sulphonate. Moreover the solid obtained had a purity of about 60% only, and in addition about 17% further product remained dissolved in the liquid fraction from which it was recoverable inconveniently by distillation.

Subsequent to the priority date of the present invention, in European Patent Application No. 164 786 to Shell, published on 18th Dec. 1985, there is disclosed reaction between a branched chain acyl chloride and potassium phenol sulphonate in an organic solvent, preferably an aromatic hydrocarbon at elevated temperature. The specification neither explicitly discloses the combination of selecting aliphatic hydrocarbons as solvent in conjunction with linear acyl chloride reactants nor does it imply that benefit can be obtained thereby.

It is an object of the present invention to provide a process for reacting an acyl halide with a phenol sulphonate salt in the presence of a solvent in which one or more of the problems or difficulties mentioned hereinbefore are ameliorated or avoided. It is a further object of at least some embodiments to produce a readily separated solid product in a high or improved yield having a high or improved purity. Other and further objects of some or other embodiments of the invention may become apparent during the course of the description.

According to the present invention there is provided a process for the preparation of acyloxybenzene sulphonate salts in which an alkali metal phenol sulphonate is reacted with an aliphatic acyl halide at an elevated temperature in the presence of an organic solvent, forming a reaction mixture from which alkali metal acyl oxybenzene sulphonate salts precipitate as a separable solid characterised in that the acyl chloride is linear, containing at least 6 carbon atoms, the solvent is selected from aliphatic hydrocarbons and has a boiling point of at least 130° C. and the reaction is carried out at a temperature selected in the range of at least 130° C. to 200° C.

Advantageously, it has been found that by selecting such solvents and linear acyl chloride reagent it is possible to obtain an extremely high or improved yield of acyloxybenzene sulphonate salt that is readily separable from a reaction mixture that remains mobile and liquid throughout the course of the reaction, thereby enabling clean and rapid evolution of gas from the reaction mixture. As a consequence of obtaining the product in such good yield, the residue of phenol sulphonate reactant, which is often the major impurity in the product, is reduced to very low proportions so that the product has improved purity also.

The phenol sulphonate reagent can have the hydroxyl and sulphonate substituents in any positions relative to each other around the benzene nucleus and can employ any alkali metal salt. However, it is especially useful to employ the sodium salt of the compound in which the sulphonate substituent is para to the hydroxyl substituent which compound is meant, hereinafter, where reference is made to sodium phenol sulphonate (SPS for short). The phenol sulphonates are preferably anhydrous or substantially anhydrous.

It is especially suitable to employ a linear aliphatic acyl chloride containing from 6 to 15 carbon atoms, and particularly 6 to 10 carbom atoms, including specifically the acid chlorides of heptanoic acid, octanoic acid, nonanoic acid and decanoic acid. Such acyl chlorides have boiling points that permit reaction temperatures in excess of 130° C. to be employed. It has been found for such straight chain reactants that under the conditions of the present invention, yields and purities well in excess of 90% by weight based upon the phenol sulphonate can be obtained. It has been found that if branched chain acyl chlorides of similar molecular weight such as 3,5,5-trimethyl hexanoic acid or 2-ethyl hexanoic acid were alternatively employed, by virtue of their comparatively lower reactivity, a lower purity and yield is normally obtained than for the straight chain compound. Moreover, it is also relevant to point out that whereas for branched chain acyl chlorides there is no difference in yield between aromatic and aliphatic hydrocarbon solvents, there is a very distinct benefit in the yield from linear acyl chlorides by selecting the aliphatic hydrocarbons.

The total amount of acyl halide, such as the acyl chloride employed is greater than one mole per mole of phenol sulphonate, and by virtue of the fact that the liquid phase containing it can be physically separated from the product at the end of the reaction, it is preferable to employ at least 1.2 moles per mole and especially from 1.5 to 5 moles per mole. The use of a substantial excess maximises the extent to which the insoluble reactant, the phenol sulphonate, can react and thereby improves both yield and purity of the product.

The reaction between the acyl halide and the phenol sulphonate generates one mole of hydrogen halide per mole of each reactant consumed. In order to regularise and control the evolution of the hydrogen chloride or hydrogen bromide gas, it is preferable to introduce at least part of the acyl halide progressively into a reaction mixture containing the particulate phenol sulphonate suspended in the organic solvent. Such a mixture, advantageously is stirrable at all times during the reaction. Such introduction advantageously occurs over a period of from 0.5 to 5 hours. At the end of the introduction of acyl chloride or bromide, the reaction mixture can be permitted to continue reacting for a further period of up to 5 hours under normal circumstances and in practice the total reaction period during and post acyl halide introduction lasts often from 1.5 to 6 hours.

During the reaction between acyl halide and phenol sulphonate, it is desirable to sparge the reaction medium with an inert gas such as nitrogen in order to facilitate the removal from the medium of e.g. hydrogen chloride and to promote good mixing of the solid phenol sulphonate with the acyl halide. Sparging is assisted by choice of especially aliphatic hydrocarbons or mixtures containing only a low proportion of aromatic hydrocarbon, so as to suppress any tendency of the mixture to form a gelatinous product which can induce excessive foaming of the mixture with the consequential problems of control, likelihood of ejection of product from the reaction vessel and increased hazard.

The solvent employed according to the present invention can be any single aliphatic hydrocarbon having a boiling point of at least 130° C. normally up to 250° C. or, more conveniently, can be mixtures of aliphatic hydrocarbons of the appropriately high boiling point such as those obtained as fractions or cuts from the distillation of mineral oils. Cuts, having a median boiling point in the range of from about 140 ° to about 210° C. have been found to be extremely satisfactory. The solvent need not be 100% aliphatic, but a minor proportion can be aromatic, provided that it still meets the criterion of boiling at over 130° C. The proportion is preferably less than 25% v/v and particularly less than 10% v/v.

If it is of practical benefit to employ enough solvent that the reaction mixture is always stirrable. Preferably the solvent weighs at least as much as the weight of phenol sulphonate, and more preferably is from one and a half to five times the weight of the phenol sulphonate. In many embodiments, this corresponds to a weight ratio of solvent to excess unreacted acyl chloride at the end of the reaction period is in the range of 3:1 to 5:1. When a mole ratio of about 2:1 acyl chloride:phenol sulphonate is used, but will be higher if a lower ratio such as 1.5:1 is used.

It is especially suitable to employ a reaction temperature of from 135 ° to 175° C., since by so doing the rate of reaction is maximised, which is of particular importance in the reactivity of branched acyl chlorides, whilst at the same time the likelihood of charring and production of a tar or oil is substantially eliminated.

The product can be conveniently separated from the reaction mixture by conventional solid/liquid separation apparatus such as a centrifuge, and the liquor can be recycled. The solid product retains inevitably some liquor. This can be removed by washing with acetone. Since the bulk of the liquor retained in the cake consists of relatively cheap solvent there is a considerably reduced incentive to recover and recycle the liquor from any washings of the product cake, but to maximise efficiency of acid chloride usage this may be done, if desired. In addition, since the solvent is essentially nonpolar the propensity of the liquor to retain the hydrogen chloride is considerably reduced, with the result that product has a reduced ionisable chloride impurity content.

Sodium phenol sulphonate is often available as the dihydrate, whereas references in the prior art to the use of phenol sulphonates have indicated that they should advantageously be anhydrous so as to minimise the wasteful conversion of acyl chloride to carboxylic acid. It has been found that by appropriately heating an hydrated phenol sulphonate, and in particular sodium phenol sulphonate with certain aliphatic or aromatic hydrocarbons having boiling points in excess of 130° C., a mixture of water and hydrocarbon can be boiled off together which subsequently separates into two immiscible phases. This is an effective technique for small scale preparations.

It has been found that when the water content of the phenol sulphonate salt has been reduced by such a water/solvent co-removal technique, to a content of from 0.1 to 1% by weight, the resultant salt has the capability of producing on reaction with linear acyl halide an acyloxybenzene sulphonate salt of great purity and/or in high yield (based on the sulphonate salt) which may be better than if the sulphonate salt had been dried by heating in air. Whilst it is believed that such a residual amount of water may itself be responsible for the improvement, acting in some way as a catalyst, the observation is not limited to such a belief, and it is recognised that the water content may be a measurable indicator of the extent to which the phenol sulphonate salt dried in such a manner, is suited to subsequent esterification. In many instances, water removal with solvent is halted when the residual water content of the salt has been lowered to 0.2% to 0.5% by weight of the salt.

It is especially beneficial to select as the organic solvent for coremoval of water from phenol sulphonate, the aliphatic solvent since by so doing the benefit of employing an aliphatic solvent can be aggregated with the benefit of pre-azeotroping to retain only a controlled amount of water in the phenol sulphonate starting material, especially in the context of reacting there-with a straight chain acyl chloride such as nonanoyl chloride.

It will be recognised that the technique of co-removing water and solvent from hydrated phenol sulphonate represents a convenient method not available if solvents such as toluene are employed, which for example with SPS leaves 4% water, an excessive amount that causes undue degradation of acyl chloride to acid in the subsequent esterification reaction mixture. The removal of the mixture of water and hydrocarbon at atmospheric pressure tends to begin at a temperature within the range of 105° to 110° C. and continues until the boiling point of the solvent is nearly reached. Accordingly, the progress of the water removal can be followed by observation or monitoring of the boiling point of the mixture. It is an excellent indication that the water removal is substantially complete, i.e., leaves a residue of 0.1 to 1.0% water when the boiling temperature of mixture rises to within about 5° to 10° C. of the solvent boiling point. At that point, acyl halide reactant can be introduced and the esterification stage be carried out, possibly with the addition of further solvent or the remaining solvent can be separated from the dried phenol sulphonate salt and recycled for drying of further salt whilst the salt is contacted with recycled excess acyl halide/solvent mixture replenished as necessary with some fresh acyl halide and solvent to carry out the esterification.

When acyl chloride is used, the acyl chloride reactant need not be 100% pure but can tolerate a small residue of hydrogen chloride without significant or substantial impairment of the esterification process.

The esters produced in the present invention are suitable, in particular, as generators of peroxyacids in aqueous alkaline media on reaction with hydrogen peroxide and thus can be readily incorporated in solid bleaching or washing compositions also containing a persalt or used with compositions containing a persalt or hydrogen peroxide, thereby providing a low temperature bleaching system.

Having described in general terms the two aspects of the present invention, specific embodiments and comparisons will be described in greater detail by way of exemplification.

COMPARISONS 1-5 AND RUNS 6 TO 12

In comparisons C1–C5, attempts were made to employ various solvents named in prior publications as solvents for use in the reaction between an acyl chloride and a phenol sulphonate salt. In each comparison, sodium phenol sulphonate (laboratory grade from BDH), was introduced into a glass vessel equipped with a reflux condenser, stirrer an inlet for acyl chloride, and containing 277 mls of ethylene dichloride, (EDC) 1,4-dioxan (dioxan) or toluene, unless otherwise stated. The named acid chloride was then introduced gradually into the reaction vessel whilst maintaining the mixture refluxing or at the elevated temperature over a period of about 90 minutes. Thereafter, reaction was allowed to continue for a further 2½ hours at the same temperature, except in C5, and the resultant solid was filtered off under vacuum washed with acetone and dried. The product was then analysed for sodium alkanoyl oxybenzene sulphonate, and the results are expressed in Table 1 below as yield based upon the theoretical esterification of all the phenol sulphonate and purity being the proportion of the ester in the prod.uct. Table 1 also summarises the weight of sodium phenol sulphonate and mole ratio thereto of acid chloride that is introduced (AC:SPS). INN represents 3,5,5-trimethyl hexanoic acid chloride and NON nonanoic acid chloride respectively. In the C5 nonanoic acid chloride was introduced at 80° C. and the temperature after introduction was increased to 100° C.

The same procedure was followed for runs C6, C9 and 10 to 12 which employed either a mixture of Shellsol AB and Solvesso 150 (SHELLSOL and SOLVESSO are Trade Marks) designated SS, all comparisons or SHELLSOL D40, designated SD. Where R follows the designation in Table 1, it indicates that the liquor into which the batch of phenol sulphonate was introduced comprised residual solvent/residual acid chloride which had been separated from a previous batch of product, and only the supplementary amount of acid chloride was introduced gradually to reach the final mole ratio of 2:1.

TABLE 1

|  | Solvent | Weight SPS (g) | Acid chloride | Mole Ratio AC:SPS | Reaction Temp °C. | Purity % | Yield % |
| --- | --- | --- | --- | --- | --- | --- | --- |
| C1 | EDC | 80 | INN | 2:1 | 85 | 25.1 | 17.4 |
| C2 | Dioxan | 80 | INN | 2:1 | 102 | 60.0 | 24.6 |
| C3 | Toluene | 80 | INN | 2:1 | 115 | 1.5 | 0.9 |
| C4 | Toluene | 80 | NON | 2:1 | 110 | 58.8 | 45.8 |
| C5 | Toluene | 102 | NON | 1.3:1 | 100 | 60.9 | 47.2 |
| C6 | SS | 80 | INN | 2:1 | 180 | 85.9 | 74.9 |
| C7 | SS R1 | 80 | INN | 2:1 | 180 | 79.5 | 70.0 |
| C8 | SD | 80 | INN | 2:1 | 175 | 77.3 | 72.0 |
| C9 | SS | 80 | NON | 2:1 | 175 | 84.5 | 78.4 |
| 10 | SD | 72 | NON | 1.5:1 | 165 | 94.5 | 92.5 |
| 11 | SD | 80 | NON | 2:1 | 168 | 96.8 | 94.8 |
| 12 | SD/R1 | 80 | NON | 2:1 | 168 | 96.6 | 94.9 |

From Table 1, it can be seen that in the prior art solvents, the yield and purity of the ester product ranged from virtually non-existent to poor. Whilst there was some improvement in employing the principally aromatic hydrocarbon Solvesso/Shellsol AB solvent, the yield and purity of the esters from both linear and branched chain acyl chlorides was still below acceptable levels. When the branched chain acyl chlorides were used in aliphatic hydrocarbon solvents no improvement was detected, but for linear acyl chloride the best results were obtained using as solvent Shellsol D40 which is principally aliphatic, comprising a mixture of hydrocarbons boiling from 162° to 197° C., median 169° C. It will be observed that the solvent/excess acyl chloride could be readily recycled.

EXAMPLES 13-15

In these Examples, the process employed a first stage in which sodium phenol sulphonate dihydrate was dried by co-removal of water and the same solvent as subsequently used in the esterification process followed by secondly an esterification stage conducted in similar manner to earlier runs, except that the total reaction time was shortened to 2½ hours in Ex 13 and 14 and 3 hours in Ex 15 and in all three the reaction mixture in the second stage was sparged with nitrogen. In Ex 13 the acyl chloride was laboratory grade reagent, in Ex 14 it was the distilled product obtained by reaction between thionyl chloride and nonanoic acid in a process catalysed by dimethyl formamide and in Ex 15 the same acid chloride product was used but without an intervening distillation stage. In each of these Examples the solvent (SD) was present in a ratio to the phenol sulphonate salt of about 2.15 mls solvent per g salt.

The first stage in these Examples was carried out by heating the phenol sulphonate containing about 15% w/w water with twice its weight of SHELLSOL D40 solvent. A mixture of water and solvent started to boil off at about 105° C. and on condensation into a receiving flask separated into two distinct phases separable by running off the lower aqueous phase. Sufficient water had been removed when the boiling point of the mixture reached about 160° C.

The process oonditions and product analyses are summarised in Table 2.

TABLE 2

|  | Solvent | Weight SPS (g) | Acid chloride | Mole Ratio AC:SPS | Reaction Temp °C. | Purity % | Yield % |
|---|---|---|---|---|---|---|---|
| Ex 13 | SD | 94.6 | NON | 2:1 | 170 | 99.3 | 99.3 |
| Ex 14 | SD | 261.6 | NON | 2:1 | 165 | 99.3 | 99.4 |
| Ex 15 | SD | 94.6 | NON | 2:1 | 167 | 99.2 | 99.2 |

From Table 2, it can be seen that removing water from the phenol sulphonate by co-removal with hydrocarbon solvent but leaving a very small residue of water resulted in the preparation of a product having the highest yield and purity of all, and secondly that a reaction time of 2½ hours was practical. Comparison between Example 15 and 13/14 shows that an intervening distillation stage in the manufacture of acyl chloride is an unnecessary step since the purity and yield of the product remained substantially the same without the step.

We claim:

1. In a process for the preparation of acyloxybenzene sulphonate salts in which an alkali metal phenol sulphonate is reacted with an alkanoyl halide at an elevated temperature in the presence of an organic solvent, forming a reaction mixture from which alkali metal alkanoyl oxybenzene sulphonate salts precipitate as a separable solid, the improvement wherein the alkanoyl halide is a linear alkanoyl chloride containing from 6-10 carbon atoms, the solvent is selected from aliphatic hydrocarbons and has a boiling point of at least 130° C., and the reaction is carried out at a temperature selected in the range of 130° C. to 200° C.

2. A process according to claim 1 in which the alkanoyl chloride is the chloride of an acid selected from the group consisting of heptanoic, octanoic, nonanoic and decanoic.

3. A process according to claim 2 in which the alkanoyl chloride is nonanoyl chloride.

4. A process according to claim 1 in which the solvent has a median boiling point of about 140 to 210° C.

5. A process according to claim 1 in which the alkanoyl chloride and phenol sulphonate salt are contacted in a mole ratio of at least 1.5 to 1.

6. A process according to claim 1 in which the total reaction period for alkanoyl chloride and phenol sulphonate salt lasts from 1.5 to 6 hours.

7. A process according to claim 1 in which the reaction temperature is from 135 to 175° C.

8. A process according to claim 1 in which said alkali metal sulphonate is sodium phenol sulphonate which has been dried to a water content of 0.1 to 1% by co-removing water therefrom by boiling with a hydrocarbon boiling above 130° C.

9. A process according to claim 5 in which a linear C6-C10 alkanoyl chloride and sodium phenol sulphonate are contacted at a temperature of 135 to 175° C. in an aliphatic solvent having a median boiling point of about 140 to 210° C.

10. A process according to claim 4 in which said hydrocarbons have a median boiling point of about 140 to 170° C.

11. A process according to claim 5 wherein said mole ratio is not more than 5:1.

12. A process according to claim 9 in which said aliphatic solvent has a median boiling point of about 140° to 170° C.

* * * * *